United States Patent [19]
Lavaud

[11] Patent Number: 5,914,117
[45] Date of Patent: Jun. 22, 1999

[54] COSMETIC COMPOSITION CONTAINING A MONOESTER OF A $C_4$-$C_{10}$ ACID AND OF A $C_{16}$-$C_{18}$ ALCOHOL AND HOLLOW PARTICLES

[75] Inventor: Brigitte Lavaud, Paris, France

[73] Assignee: L'Oreal, Paris, France

[21] Appl. No.: 08/738,109

[22] Filed: Oct. 25, 1996

[30] Foreign Application Priority Data

Oct. 25, 1995 [FR] France .................. 95 12584

[51] Int. Cl.⁶ .................. A61K 7/48; A61K 7/06; A61K 7/15
[52] U.S. Cl. .................. 424/401; 424/45; 424/47; 424/70.1; 424/70.11; 424/78.03; 424/497; 514/844; 514/937; 514/944; 514/945
[58] Field of Search .................. 424/401, 497, 424/45, 47, 70.11, 70.1, 78.03; 514/844, 937, 944, 945

[56] References Cited

U.S. PATENT DOCUMENTS

| | | |
|---|---|---|
| 3,541,581 | 11/1970 | Monson . |
| 3,615,972 | 10/1971 | Morehouse et al. . |
| 5,219,561 | 6/1993 | Gagnebien et al. . |
| 5,456,863 | 10/1995 | Bergmann . |
| 5,532,000 | 7/1996 | Kauffmann . |
| 5,637,291 | 6/1997 | Bara et al. . |
| 5,660,839 | 8/1997 | Allec et al. . |
| 5,690,945 | 11/1997 | Bui-Bertrand et al. . |

FOREIGN PATENT DOCUMENTS

| | | |
|---|---|---|
| A-0447286 | 9/1991 | European Pat. Off. . |
| A-0452202 | 10/1991 | European Pat. Off. . |
| A-0463962 | 1/1992 | European Pat. Off. . |
| 0 566 442 | 10/1993 | European Pat. Off. . |
| A-4221914 | 1/1994 | Germany . |

OTHER PUBLICATIONS

English language Derwent Abstract of EP–A–0452202.
English language Derwent Abstract of EP–A–0463962.
English language Derwent Abstract of DE–A–4221914.
English language Derwent Abstract of JP–A–60184004.

Primary Examiner—Thurman K. Page
Assistant Examiner—Brian K. Seidleck
Attorney, Agent, or Firm—Finnegan, Henderson, Farabow, Garrett & Dunner, L.L.P.

[57] ABSTRACT

A cosmetic composition for the skin, including the scalp, comprising (a) at least one specific ester which is a monoester of a $C_4$–$C_{10}$ aliphatic acid and a $C_{16}$–$C_{18}$ aliphatic alcohol, and (b) hollow particles exhibiting a mean particle size ranging from 1 μm to 300 μm. This composition can be used as face cleanser, deodorant, and, in particular, as a shaving product.

29 Claims, No Drawings

COSMETIC COMPOSITION CONTAINING A MONOESTER OF A $C_4$-$C_{10}$ ACID AND OF A $C_{16}$-$C_{18}$ ALCOHOL AND HOLLOW PARTICLES

The present invention relates to a new cosmetic composition for the skin, including the scalp, and in particular for shaving, but which can also be used as face cleanser (scrub cleanser) or deodorant, and which comprises (a) at least one specific ester which is a monoester of a $C_4$–$C_{10}$ aliphatic acid and a $C_{16}$–$C_{18}$ aliphatic alcohol, and (b) hollow particles exhibiting a mean particle size ranging from 1 $\mu$m to 300 $\mu$m.

The products used by human beings for removing body hairs for aesthetic or hygienic reasons are well known and varied, from shaving soap in powder, bar or cake form to shaving creams and foams and to aqueous shaving gels (reference should be made, in this respect, to the article entitled "Shaving Preparations—Origin of Shaving and Sales Trends," by Robert E. Sauté, published in the work "The Chemistry and Manufacture of Cosmetics," Second Edition, 1975, Vol. IV, chapter 64, pages 1313 to 1341, by Maison G. de Navarre, the full disclosure of which article is incorporated herein by reference).

In addition to conventional shaving gels, shaving gels with delayed foaming, (or with a delayed foam effect) are already known and have been more precisely described in many patents, such as, for example, U.S. Pat. No. 3,541,581, U.S. Pat. No. 4,405,489 and French Patent No. 2,595,943, the full disclosure of each of which is incorporated herein by reference.

These gels with a delayed foam effect are compositions which are generally packaged under pressure in an aerosol device which, under the effect of a propellent, delivers gels which are nonfoaming under static conditions but which, under the mechanical action due to the spreading of the product on the skin, spontaneously and virtually instantaneously produce a foam on the skin.

Shaving gels with delayed foaming must combine numerous characteristics which make their development particularly difficult.

First of all, the gel delivered into the hand must exhibit an appropriate rheology, i.e., rigidity and consistency. In addition, when spread onto the skin of the face, this gel must be capable of very rapidly developing a foam, itself capable of acquiring volume without, however, producing small accumulations of rigid foam. Finally, the foam generated by the gel must be endowed with good cosmetic qualities, such as moisturization, contribution of softness and the absence of a sticky effect and/or a runny effect on the skin.

Unfortunately, the delayed-foaming shaving gel compositions of the prior art do not optimize all these conditions.

To facilitate the use and to increase the stability of such gels, it has already been proposed to introduce therein alkanolamides of $C_{12}$–$C_{18}$ fatty acids or ethoxylated fatty alcohols, or else propylene glycol dipelargonate. In such cases, however, the gels obtained have not optimized all the properties listed above and have therefore not yet been found completely satisfactory.

The disadvantages mentioned above are also true for other types of gels, shaving foams, face cleansing products and deodorants.

The present invention aims to provide cosmetic compositions, in particular shaving compositions, and more particularly shaving gels with delayed foaming, and shaving creams and foams exhibiting improved properties.

Thus, after numerous investigations directed to this question, the Inventor has discovered, completely unexpectedly and surprisingly, that by adding a monoester of a $C_4$–$C_{10}$ aliphatic acid and of a $C_{16}$–$C_{18}$ aliphatic alcohol and hollow particles exhibiting a mean particle size ranging from 1 $\mu$m to 300 $\mu$m, to a cosmetic composition for the skin, it was possible to obtain a composition, and in particular a shaving composition, exhibiting improved performance and/or properties, and in particular exhibiting improvements in the desired characteristics described above. This discovery underlies the present invention.

A subject of the present invention is thus a new cosmetic composition for the skin, including the scalp, which comprises (a) at least one monoester of a $C_4$–$C_{10}$ aliphatic acid and a $C_{16}$–$C_{18}$ aliphatic alcohol, and (b) hollow particles exhibiting a mean particle size ranging from 1 $\mu$m to 300 $\mu$m.

Another subject of the invention is a shaving composition of the type comprising a water-soluble soap and (a) at least one monoester of a $C_4$–$C_{10}$ aliphatic acid and a $C_{16}$–$C_{18}$ aliphatic alcohol, and (b) hollow particles exhibiting a mean particle size ranging from 1 $\mu$m to 150 $\mu$m.

The present invention is also directed to the use of the compositions described above for shaving hair present on human or animal skin. The present invention is additionally directed to the use of such a composition as, or for the manufacture of, a deodorant cosmetic composition.

The monoester(s) of $C_4$–$C_{10}$ aliphatic acids and of $C_{16}$–$C_{18}$ aliphatic alcohols which may be employed according to the invention are preferably chosen from the monoesters of $C_4$–$C_{10}$ linear or branched saturated aliphatic acids and of $C_{16}$–$C_{18}$ linear saturated aliphatic alcohols.

Monoesters of this type which are more particularly preferred according to the present invention are the ester of heptanoic acid and of stearyl alcohol (or stearyl heptanoate), the ester of octanoic acid and of stearyl alcohol (or stearyl octanoate) or stearyl heptanoate/octanoate mixtures, in particular the stearyl heptanoate (67%)/octanoate (33%) mixture sold, for example, by the company Croda under the trade name Crodamol W or by the company Stéarineries Dubois under the trade name Dub Solide.

The "hollow" particles of the invention are structurally hollow. In accordance with the invention, the term "structurally hollow" nonetheless allows the hollow particles to contain at least one additional material therein. Such additional material is preferably selected from hydrocarbons, in particular, isobutane, and isopentane, and from air and nitrogen. Often such an additional material is present in the hollow particles as a result of the process for manufacturing the hollow particles.

The hollow particles which can be used according to the invention preferably exhibit a mean particle size ranging from 5 $\mu$m to 200 $\mu$m, more preferably from 10 $\mu$m to 100 $\mu$m, and still more preferably from 50 $\mu$m to 60 $\mu$m. In the specific case of a shaving composition, the particle size preferably ranges from 1 to 150 $\mu$m, more preferably from 10 to 100 $\mu$m, and still more preferably from 15 to 60 $\mu$m.

The hollow particles are preferably made of thermoplastic materials such as polyamides, for example nylon, or polymers or copolymers of acrylonitrile, vinylidene chloride, vinyl chloride and/or an acrylic or styrene monomer, which are optionally expanded. The acrylic monomer is, for example, preferably a methyl or ethyl acrylate or methacrylate. The styrene monomer is, for example, preferably α-methylstyrene or styrene.

"Orgasol" particles sold by the company Atochem can be used as hollow nylon particles. These particles are solid porous spheres with a diameter ranging from 5 $\mu$m to 60 $\mu$m.

The particles are more preferably hollow particles of an expanded vinylidene chloride and acrylonitrile copolymer or of an expanded vinylidene chloride, acrylonitrile and methacrylate terpolymer. It is possible, for example, to use a terpolymer containing: from 0% to 60% of units derived from vinylidene chloride, from 20% to 90% of units derived from acrylonitrile and from 0% to 50% of units derived from an acrylic or styrene monomer, the sum of the percentages (by weight) being equal to 100. These particles can be dry or hydrated and are, for example, those sold under the trademark Expancel by the company Nobel Casco, and in particular under references 551 DE (particle size of approximately 50 $\mu$m and density of approximately 35 kg/m$^3$), 551 DE 12 (particle size of approximately 12 $\mu$m and density of approximately 40 kg/m$^3$), 551 DE 20 (particle size of approximately 30 $\mu$m and density of approximately 65 kg/m$^3$), 551 DE 50 (particle size of approximately 40 $\mu$m), 461 DE 50 and 642 WE 50 with a particle size of approximately 50 $\mu$m and 551 DE 80 (particle size of approximately 80 $\mu$m).

It is also possible to use particles of the same terpolymer having a particle size of approximately 18 $\mu$m and a density of approximately 60 to 90 kg/m$^3$ or else a particle size of approximately 34 $\mu$m and a density of approximately 20 kg/m$^3$.

It is additionally possible to use particles of a non-expanded vinylidene chloride and acrylonitrile copolymer or of a non-expanded vinylidene chloride, acrylonitrile and methacrylate terpolymer, such as those sold under the trademark Expancel with reference 551 DU 10 (particle size of approximately 10 $\mu$m) or 461 DU 15 (particle size of approximately 15 $\mu$m).

Mention may also preferably be made, as other hollow polymeric particles which can be used according to the invention, of polymers and copolymers obtained from esters, such as, for example, vinyl acetate or lactate, or acids, such as, for example, itaconic, citraconic, maleic or fumaric acids. See, in this regard, Japanese Patent Application No. JP-A-2-112304, the full disclosure of which is incorporated herein by reference.

According to another advantageous characteristic of the invention, the particles are provided in the form of beads. It is, however, possible to use particles having the form of fibers or of needles.

The particles sold under the trademark Expancel, according to the invention, can be obtained, for example, according to the processes of Patents and Patent Applications EP-56 219, EP-348 372, EP-486 080, EP-320 473, EP-112 807 and U.S. Pat. No. -3,615,972, the full disclosure of each of which is incorporated herein by reference. The internal cavity of the hollow particles, as explained above, can contain a gas which can be air, nitrogen or a hydrocarbon, such as isobutane or isopentane.

The other constituents forming part of the compositions of the invention, and in particular the shaving products, are products which are already known per se in the art. See, in this context, the Robert E. Sauté reference mentioned above, and more precisely for shaving gels with a delayed foam effect, see, EP-A-259 843, U.S. Pat. No. 3,541,581 and FR 2 595 943, the full disclosure of which is incorporated herein by reference. For cleansing and scrub compositions, reference may be made to French Patent No. FR 2 700 952, the full disclosure of which is incorporated herein by reference, and, for deodorant products, reference may be made to the "Cosmetic Science and Technology Series", 1988, Volume 7, the full disclosure of which is incorporated herein by reference.

The water-soluble soap used in accordance with the present invention is preferably a water-soluble fatty acid salt. Such soaps are well known in the prior art, exist in the trade or can be prepared according to conventional methods, for example by the reaction of a base, such as triethanolamine, sodium hydroxide or potassium hydroxide, directly with a fatty acid, such as a $C_{10}$ to $C_{22}$ saturated or unsaturated fatty acid, or mixtures of these acids. Preferred soaps according to the invention include water-soluble stearates, myristates and palmitates, such as the soluble soaps of commercial stearic or palmitic acids. The sodium and potassium salts of these acids and their mixtures are preferably used for shaving soaps, creams and foams and the triethanolamine salts of these acids are more particularly preferred for shaving gels. It is well known, furthermore, that the commercial product sold under the name of stearic acid may be a mixture of stearic and palmitic acids. The term "stearates" denotes the soaps of commercial stearic acid, but may also denote the soaps of pure stearic acid.

A water-soluble soap which is particularly preferred according to the invention for shaving gels with a delayed foam effect is triethanolamine palmitate.

A water-soluble gelling polymer can be employed according to the invention for stabilizing the composition or for adjusting its consistency to the desired value. It may then be chosen from water-soluble hydroxyalkyl celluloses or natural gums such as xanthan gum. Hydroxyalkyl celluloses are manufactured from an alkyl cellulose and an alkylene oxide such as ethylene oxide or propylene oxide. Products of this type are sold under the trademarks "Klucel" and "Natrosol" in a range of varied viscosities.

A water-soluble polymer which is more particularly preferred according to the present invention is a hydroxypropyl cellulose sold under the trademark "Klucel H" or "Klucel MF" by the company Aqualon, a hydroxyethyl cellulose sold under the trademark "Natrosol 250 HHR" by the company Aqualon, or a mixture of these two celluloses.

One of the advantages associated with the present invention is that it is possible to reduce, or even eliminate, the amount of cellulose-based thickener, the excessive proportions of which are at the source of the disadvantage of stickiness on the skin.

In the shaving gels with a delayed foam effect, the delayed-foaming agent is liquid or liquefiable and volatile at the temperature of the skin. It includes saturated aliphatic hydrocarbons containing from 4 to 6 carbon atoms, such as butanes, n-butane or isobutane, pentanes such as n-pentane or isopentane, or hexane. Mixtures of these hydrocarbons may be employed to obtain the desired vapor pressure.

A delayed-foaming agent which is particularly well suited for controlling the pressure of the gel with a view towards obtaining the foam properties required for the present invention is the mixture isopentane (75% by weight)/isobutane (25% by weight).

Water, present in the shaving composition according to the invention, takes part in the required foam properties and is used to moisten the skin and to ensure suitable shaving.

In the compositions according to the present invention, in particular the shaving compositions, the monoester of a $C_4$–$C_{10}$ aliphatic acid and of a $C_{16}$–$C_{18}$ aliphatic alcohol is preferably present in weight concentrations (referred to the whole of the composition) ranging approximately from 0.1 to 5%, and more preferably ranging approximately from 1.5 to 3%. The hollow particles are preferably present in weight concentrations ranging approximately from 0.005 to 5%, and more preferably ranging approximately from 0.01 to 2%, which corresponds to a concentration by volume preferably ranging approximately from 0.07% to 150% and more preferably ranging approximately from 0.15% to 60%.

The water-soluble soap is preferably present in the shaving compositions according to the present invention in weight concentrations ranging approximately from less than 5% to more than 95%, according to the present application, to approximately 95% and more in solid soaps, to approximately 40% in creams and foams, and to approximately 20% in gels. Advantageously, an amount of soap ranging from approximately 10 to 15% is preferably used in gels with a delayed foam effect.

The water-soluble gelling polymer may be present in weight concentrations preferably ranging from approximately 0 to 3%, and more preferably ranging from approximately 0 to 1%, depending on the viscosity of the product employed.

The delayed-foaming agent (in the case of shaving gels with delayed foaming) is preferably present in weight concentrations ranging from approximately 0.5 to 10%, and more preferably from approximately 2 to 5%.

The water is preferably present in weight concentrations ranging from 0% for solid soaps to 90% for gels and, preferably, for gels, from approximately 60 to 90%.

The compositions according to the invention may further contain other ingredients or active substances which are well known in the field of cosmetic products for the chosen application, and in particular for shaving applications. Mention may be made, for example, of moisturizing agents, and among them glycerol and sorbitol; thickening agents such as allantoin or α-bisabolol; lubricants such as silicones or polydecenes; superfatting agents such as lanolin or its derivatives; emollients such as polyethylene glycol, polypropylene glycol, the benzoate of $C_{12}/C_{15}$ alcohols or polyethylene glycol and glycerol stearates; opacifying agents such as titanium oxide; surface-active agents; stabilizing agents; vitamins; solvents; dyes; fragrances; and preservatives.

Of course, the person skilled in the art will take care to choose the optional additional compound(s) mentioned above so that the advantageous properties intrinsically associated with the cosmetic composition according to the invention are not, or not substantially, detrimentally affected by the envisaged addition(s).

The creams and the gels according to the invention may be packaged in the form of tubes or aerosols, and the foams as an aerosol, according to techniques which are well known to the person skilled in the art and in particular, for gels with a delayed foam effect, as described in U.S. Pat. No. 3,541,581, the disclosure of which is incorporated herein by reference.

The aerosol devices may have a single or double container.

In the double-container aerosol devices, the propellent system is separated from the gel or cream in accordance with the invention. In fact, the gel or cream in accordance with the invention is introduced, for example, into the middle part of the double-container aerosol and the propellent is introduced into the outer container, which is separated from the middle part by a diaphragm which is a compressible plastic membrane. In such double-container devices, the propellent system may then comprise a condensable gas such as a hydrocarbon, for example propane, butane, isobutane or isopentane, halogenated hydrocarbons or dimethyl ether or mixtures of these compounds. It may also comprise a mixture of these condensable propellent agents with noncondensable gases such as nitrous oxide or nitrogen.

In single-container devices, the propellent system consists only of noncondensable gases which are insoluble in the gel in accordance with the invention, such as nitrogen, argon, neon, krypton, xenon, helium, radon, nitrous oxide or carbon dioxide. Such devices are equipped with a dip tube, into the upper part of which the said propellent system is introduced. In this case, the propellent system, which is noncondensable and insoluble in the composition in accordance with the invention, acts as a piston and expels the composition via the dip tube.

In the aerosols, the composition in the pressurized state (or "juice") advantageously represents from 90 to 98% of the weight of the whole composition, and the propellent system from 2 to 10% of this weight.

Concrete, but in no way limiting, examples illustrating the invention will now be given.

EXAMPLE 1

A shaving gel with delayed foaming was prepared in the following way:

(I) 96.5 grams of the following composition were introduced into the middle part of a double-container aerosol device:

| | |
|---|---|
| Palmitic acid | 12.5 g |
| Triethanolamine | 9.2 g |
| Glycerol | 3.9 g |
| Hydroxypropyl cellulose (Klucel MF from the company Aqualon) | 0.1 g |
| Polyethylene glycol (Polyox WSR 205 from the company Amerchol) | 0.2 g |
| Stearyl heptanoate (67%)/octanoate (33%) (Dub Solide from the company Stéarineries Dubois) | 1.9 g |
| Expanded microspheres of vinylidene chloride/acrylonitrile copolymer containing isobutane, sold under the trademark Expancel 551 DE 20 by the company Nobel Casco | 0.05 g |
| Fragrance, dye | q.s. |
| Demineralized water | q.s. for 100 g | and (ii) 3.5 grams of a delayed-foaming agent consisting of an isopentane (75% by weight)/isobutane (25% by weight) mixture.

The middle part was closed. Pressurization of the mixture obtained above or "juice" was then carried out by introducing into the lower part of the double container, and via the bottom opening, 4 to 10 grams of a propellent consisting of an isobutane (55%), butane (22%) and propane (23%) mixture (by weight) sold under the name Aérogaz 3.2N by the company Elf Aquitaine.

The crimped aerosol was then ready to be employed. When it was brought into action, it delivered into the hand a gel with a rheology such that it was given a rigidity enabling it to stay firm in the hand and to be spread easily in a homogeneous manner on the skin of the face without giving rise to small accumulations of foam. Under the mechanical action of the spreading on the skin, the gel rapidly developed a foam, which was soft on application, smooth and uniform, which did not stick to the skin and did not run. After shaving, the skin was soft and smooth.

EXAMPLE 2

A shaving cream with the following composition was prepared:

| | |
|---|---|
| Stearic acid ($C_{16}/C_{18}$ 50/50) | 2.75 g |
| Triethanolamine | 0.45 g |
| Glycerol | 5 g |

| | |
|---|---|
| Glyceryl stearate and polyethylene glycol 100 stearate sold by the company I.C.I. under the name Arlacel 165 | 5 g |
| Stearyl alcohol | 5 g |
| Stearyl heptanoate (67%)/octanoate (33%) (Dub Solide from the company Stéarineries Dubois) | 5 g |
| Expanded microspheres of vinylidene chloride/ acrylonitrile/methyl methacrylate copolymer containing isobutane sold under the trademark Expancel 551 DE by the company Nobel Casco | 0.1 g |
| Titanium oxide treated with aluminium stearate/alumina | 1 g |
| Benzoate of $C_{12}/C_{15}$ alcohols | 8 g |
| Stabilizing agent: sodium hexadecyl phosphate | 1 g |
| α-Bisabolol | 0.1 g |
| Fragrance, preservatives | q.s. |
| Demineralized water | q.s. for 100 g |

The cosmetic properties of the cream were comparable with those of the gel of Example 1.

EXAMPLE 3

A shaving foam was prepared in the following way:

(i) 96 grams of the following composition were introduced, via the neck, into an aerosol can:

| | |
|---|---|
| Stearic acid ($C_{16}/C_{18}$ 50/50) | 7.9 g |
| Triethanolamine | 2.9 g |
| Glycerol | 2.5 g |
| Coconut fatty acid | 0.6 g |
| KOH as a 50% aqueous solution | 0.4 g AM* |
| Stearyl heptanoate (67%)/octanoate (33%) (Dub Solide from the company Stéarineries Dubois) | 0.5 g |
| Expanded microspheres of vinylidene chloride/ acrylonitrile/methyl methacrylate copolymer containing isobutane sold under the trademark Expancel 551 DE 20 by the company Nobel Casco | 0.3 g |
| Sorbitan monolaurate containing 20 mol of ethylene oxide | 0.96 g |
| Cationic polymer (dimethyldiallylammonium chloride/acrylamide 50/50 copolymer as an aqueous solution containing 8% of AM, sold under the trade name Merquat S by the company Merck) | 0.23 g AM* |
| Mixture of isopropanolamine cocoate and lanolate as a 47% aqueous solution | 0.9 g AM* |
| Fragrance, preservatives | q.s. |
| Demineralized water | q.s. for 100 g |

*AM denotes Active Material.

After positioning the valve and crimping onto the can, (ii) 4 grams of a propellent composed of an isobutane (55%), butane (22%) and propane (23%) mixture (by weight) sold under the name Aérogaz 3.2N by the company Elf Aquitaine were introduced via the valve.

The cosmetic properties of the shaving foam were comparable with those of the gel of Example 1.

EXAMPLE 4

A deodorant stick with the following composition was prepared:

| | |
|---|---|
| Butyl alcohol containing 14 mol of propylene oxide | 15 g |
| Isopropyl palmitate | 5 g |
| Stearyl heptanoate (67%)/octanoate (33%) (Dub Solide from the company Stéarineries Dubois) | 4 g |
| Stearyl alcohol | 19 g |
| Hydrogenated castor oil | 2 g |
| Micronized anhydrous aluminium chlorohydrate | 15 g |
| Talc (magnesium silicate) | 2 g |
| Expanded microspheres of vinylidene chloride/ acrylonitrile/methyl methacrylate copolymer containing isobutane sold under the trademark Expancel 551 DE 20 by the company Nobel Casco | 0.7 g |
| Preservative, fragrance | q.s. |
| Silicone oil: D.C. 345 Fluid from the company Dow Corning | q.s for 100 g |

This stick left the skin soft and nonsticky.

What is claimed is:

1. A cosmetic composition for the skin, which comprises:
   (a) at least one monoester of a $C_4$–$C_{10}$ aliphatic acid and a $C_{16}$–$C_{18}$ aliphatic alcohol, and
   (b) hollow particles exhibiting a mean particle size ranging from 1 μm to 300 μm.

2. A cosmetic composition according to claim 1, for use in shaving, which additionally comprises at least one water-soluble soap.

3. A cosmetic composition according to claim 1, wherein said at least one monoester is a stearyl heptanoate or a stearyl octanoate.

4. A cosmetic composition according to claim 1, wherein said at least one monoester is a stearyl heptanoate/octanoate mixture.

5. A cosmetic composition according to claim 1, wherein said hollow particles are formed from a thermoplastic material.

6. A cosmetic composition according to claim 5, wherein said thermoplastic material is nylon or a polymer or copolymer of at least one monomer selected from the group consisting of vinylidene chloride, vinyl chloride, acrylonitrile, acrylic and styrene.

7. A cosmetic composition according to claim 6, wherein said thermoplastic material is selected from an expanded copolymer formed from at least two monomers selected from the group consisting vinylidene chloride, vinyl chloride, acrylonitrile, acrylic and styrene.

8. A cosmetic composition according to claim 1, wherein said hollow particles exhibit a mean particle size ranging from 10 μm to 100 μm.

9. A shaving composition according to claim 2, wherein said at least one soap is a salt of stearic, myristic or palmitic acid.

10. A cosmetic composition according to claim 1, wherein said at least one monoester is present in a weight concentration ranging from 0.1 to 5% by weight with respect to the total weight of the composition.

11. A cosmetic composition according to claim 10, wherein said at least one monoester is present in a weight concentration ranging from 1.5 to 3% by weight with respect to the total weight of the composition.

12. A cosmetic composition according to claim 1, wherein said hollow particles are present in a weight concentration ranging from 0.005% to 5% by weight with respect to the total weight of the composition.

13. A cosmetic composition according to claim 12, wherein said hollow particles are present in a weight concentration ranging from 0.01% to 2% by weight with respect to the total weight of the composition.

14. A cosmetic composition according to claim 1, which is provided in the form of a solid or liquid soap, a cream, a gel or a foam.

15. A shaving composition according to claim 2, which is provided in the form of an aqueous shaving gel with a delayed foam effect and additionally comprises at least one volatile foaming agent in an amount sufficient to impart said delayed foam effect, wherein said at least one volatile foaming agent is a butane, a pentane or a hexane.

16. A gel according to claim 15, wherein said at least one volatile foaming agent is a mixture of isopentane and isobutane.

17. A gel according to claim 15, wherein said at least one volatile foaming agent is present in a weight concentration ranging from 0.5 to 10% with respect to the total weight of the composition.

18. A gel according to claim 17, wherein said at least one volatile foaming agent is present in a weight concentration ranging from 2 to 5% with respect to the total weight of the composition.

19. A gel according to claim 15, which is provided in a pressurized state in the form of an aerosol.

20. A method for shaving hair, which comprises applying to said hair a shaving composition according to claim 2, and subsequently shaving said hair.

21. A cosmetic composition according to claim 1, further comprising a preservative or fragrance which is in the form of a deodorant stick composition.

22. A method of preparing a deodorant stick composition, comprising the steps of mixing the components of a cosmetic composition according to claim 1 and forming the composition obtained from said mixing into a stick.

23. A cosmetic composition according to claim 1, wherein said hollow particles are in the form of beads, fibers or needles.

24. A cosmetic composition according to claim 1, which further comprises at least one water-soluble gelling polymer.

25. A cosmetic composition according to claim 24, wherein said water-soluble gelling polymer is present in a weight concentration up to about 3% with respect to the total weight of the composition.

26. A shaving composition according to claim 2, wherein said water-soluble soap is present in a weight concentration ranging approximately from less than 5% to more than 95% with respect to the total weight of the composition.

27. A cosmetic composition according to claim 7, wherein said expanded copolymer is a copolymer formed from vinylidene chloride and acrylonitrile or a terpolymer formed from vinylidene chloride, acrylonitrile and methacrylate.

28. A shaving composition according to claim 9, wherein said at least one soap is triethanolamine palmitate.

29. A cosmetic composition according to claim 1, wherein said hollow particles contain isobutane.

* * * * *